United States Patent
Misu et al.

(10) Patent No.: US 8,585,777 B2
(45) Date of Patent: Nov. 19, 2013

(54) COSMETIC COMPOSITION FOR KERATIN FIBERS

(75) Inventors: Daisuke Misu, Yokohama (JP); Satoshi Kitano, Yokohama (JP); Hidetoshi Yamada, Tokyo (JP)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/391,648

(22) PCT Filed: Aug. 25, 2009

(86) PCT No.: PCT/JP2009/065143
§ 371 (c)(1),
(2), (4) Date: Mar. 22, 2012

(87) PCT Pub. No.: WO2011/024300
PCT Pub. Date: Mar. 3, 2011

(65) Prior Publication Data
US 2012/0183483 A1   Jul. 19, 2012

(51) Int. Cl.
*A61Q 5/10* (2006.01)
(52) U.S. Cl.
USPC ............ 8/405; 8/406; 8/431; 8/551; 8/584; 8/611; 8/619; 8/633
(58) Field of Classification Search
USPC ............ 8/405, 406, 431, 551, 584, 611, 619, 8/633
See application file for complete search history.

(56) References Cited

U.S. PATENT DOCUMENTS

| | | |
|---|---|---|
| 2003/0226217 A1 | 12/2003 | Bowes et al. |
| 2004/0064903 A1 | 4/2004 | Massoni |
| 2008/0010754 A1 * | 1/2008 | Bureiko et al. .................. 8/406 |
| 2009/0047230 A1 | 2/2009 | Caballero et al. |

FOREIGN PATENT DOCUMENTS

| | | |
|---|---|---|
| EP | 1 878 469 | 1/2008 |
| JP | 1 213220 | 8/1989 |
| WO | 2009 017757 | 2/2009 |

OTHER PUBLICATIONS

International Search Report Issued May 20, 2010 in PCT/JP09/65143 Filed Aug. 25, 2009.

* cited by examiner

*Primary Examiner* — Eisa Elhilo
(74) *Attorney, Agent, or Firm* — Oblon, Spivak, McClelland, Maier & Neustadt, L.L.P.

(57) ABSTRACT

The present invention relates to a cosmetic composition for keratin fibers, such as a composition for coloring hair or a composition for reshaping hair, comprising: (a) at least one phosphoric surfactant; (b) at least one non-ionic surfactant, (c) at least one polyol; (d) at least one oil; and (e) at least one alkaline agent. It is preferable that the cosmetic composition further comprises at least one higher alcohol. The present invention is useful because it does not generate odor while maintaining a level of cosmetic performance as comparable to that of conventional cosmetic compositions.

12 Claims, No Drawings

COSMETIC COMPOSITION FOR KERATIN FIBERS

This application is a National Stage of PCT/JP09/065143 filed Aug. 25, 2009.

TECHNICAL FIELD

The present invention relates to a cosmetic composition for keratin fibers such as hair. In particular, the present invention relates to a cosmetic composition for keratin fibers which produces a reduced amount of offensive odor.

BACKGROUND ART

A cosmetic composition for keratin fibers such as hair, for example, a hair coloring composition and a hair permanent waving composition, includes an alkaline agent. Very often alkaline agents have an offensive odor.

As the alkaline agent, ammonia is commonly used.

Ammonia is an excellent alkaline agent in terms of safety and performance of cosmetic treatments for keratin fibers. However, its malodor gives a strong negative influence to the usage of a cosmetic composition including ammonia for keratin fibers. Therefore, elimination of ammonia odor from the cosmetic composition is one of the important targets nowadays in the field of cosmetics for keratin fibers.

The current main method for reducing ammonia odor from a cosmetic composition for keratin fibers (this means evaporation of ammonia (odor) from the surface of the cosmetic composition) is to use another alkaline agent such as monoethanolamine instead of ammonia or to replace a part of the ammonia as disclosed in JP-A-H01-213220 (1989). However, monoethanolamine has an amine odor and this method also unfavorably affects the performance of cosmetic treatments for keratin fibers. For example, the ability to lift hair or intensively color hair, both of which are very important factors for coloring hair, is negatively affected when coloring hair using a cosmetic composition including an alkaline agent other than ammonia. In addition, the use of an alkaline agent other than ammonia sometimes causes a change in hair color, apart from the target color, which imparts a negative impact on the formula design of a cosmetic composition for coloring hair.

Accordingly, the above method is not appropriate when cosmetic performance for keratin fibers should have priority.

DISCLOSURE OF INVENTION

An objective of the present invention is to reduce the offensive odor of a cosmetic composition including an alkaline agent such as ammonia while maintaining good cosmetic performance of the cosmetic composition for keratin fibers such as hair.

The above objective of the present invention can be achieved by a cosmetic composition for keratin fibers, comprising:
(a) at least one phosphoric surfactant;
(b) at least one non-ionic surfactant;
(c) at least one polyol;
(d) at least one oil; and
(e) at least one alkaline agent.

It is preferable that the phosphoric surfactant is selected from the group consisting of monoester phosphate of alkoxylated fatty alcohol containing from 12 to 20 carbon atoms with from 1 to 50 moles of alkylene oxide selected from ethylene oxide and propylene oxide, and dialkyl phosphates of non-alkoxylated alcohol containing 12 to 22 carbon atoms, and mixtures thereof. More preferably, the phosphoric surfactant can be selected from the group consisting of a combination of ceteth-10 phosphate and dicetyl phosphate, a combination of ceteth-20 phosphate and dicetyl phosphate, and a combination of oleth-5 phosphate and dioleyl phosphate.

It is preferable that the non-ionic surfactant is selected from the group consisting of polyoxyalkylenated fatty alcohol containing from 12 to 22 carbon atoms with 1 to 50 moles of ethylene oxide, polyoxyalkylenated fatty alcohol containing from 12 to 22 carbon atoms with 1 to 50 moles of propylene oxide, and mixtures thereof.

It is preferable that the polyol is selected from the group consisting of a sugar, a sugar alcohol and a triol.

It is preferable that the oil is a non-silicone liquid fatty substance. The oil may be selected from the group consisting of liquid paraffin, liquid petroleum jelly, polydecenes, liquid esters, and mixtures thereof.

It is preferable that the alkaline agent is ammonia.

The cosmetic composition according to the present invention can further comprise at least one higher alcohol.

The cosmetic composition according to the present invention can further comprise at least one oxidation dye. The oxidation dye may be selected from oxidation bases and couplers.

The cosmetic composition according to the present invention can further comprise at least one direct dye.

The cosmetic composition according to the present invention can further comprise at least one reducing agent.

It is preferable that the cosmetic composition according to the present invention is intended for coloring keratin fibers or reshaping keratin fibers. More specifically the cosmetic composition according to the present invention is intended for coloring keratin fibers with at least one oxidation dye.

BEST MODE FOR CARRYING OUT THE INVENTION

After diligent research, the inventors have discovered that it is possible to reduce an offensive odor such as ammonia odor of a cosmetic composition for keratin fibers while maintaining good cosmetic performance of the cosmetic composition, by combining at least one phosphoric surfactant, at least one non-ionic surfactant, at least one polyol, at least one oil, and at least one alkaline agent in the cosmetic composition.

The cosmetic composition according to the present invention traps an alkaline agent such as ammonia in the composition, and the evaporation of the alkaline agent from the surface of the composition is extremely reduced. Therefore, it is not necessary to reduce the amount of an alkaline agent such as ammonia to be included in the cosmetic composition. Thus, an adequate amount of an alkaline agent can always be used. Accordingly, the cosmetic performance such as lifting keratin fibers or intensively coloring keratin fibers is not reduced or impaired in the present invention because the amount of the alkaline agent does not have to be reduced.

(Phosphoric Surfactant)

The cosmetic composition according to the present invention includes at least one phosphoric surfactant. The amount of the phosphoric surfactant(s) is not limited. The amount of the phosphoric surfactant(s) can be 0.1 wt % to 10 wt %, preferably 1 wt % to 4 wt %, relative to the total weight of the cosmetic composition.

The term "phosphoric surfactant" means a surfactant whose polar part comprises at least one phosphoric group.

The phosphoric surfactant may be of the following formula:

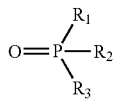

wherein
$R_1$, $R_2$ and $R_3$, which may be identical or different, represent a group chosen from:
a group —OM, in which M represents a hydrogen atom or an alkali metal, such as Na, Li or K, preferably Na or K;
a group —$OR_4$, in which $R_4$ represents a linear or branched $C_1$-$C_{40}$ alkyl group (preferably a $C_{12}$-$C_{20}$ alkyl group, and more preferably a $C_{16}$ or $C_{18}$ alkyl group), a linear or branched $C_2$-$C_{40}$ alkenyl group (preferably a $C_{12}$-$C_{20}$ alkenyl group, and more preferably a $C_{16}$ or $C_{18}$ alkenyl group), a cyclic $C_3$-$C_{40}$ alkyl group, a cyclic $C_3$-$C_{40}$ alkenyl group, a $C_5$-$C_{40}$ aromatic group, or a $C_6$-$C_{40}$ aralkyl group; and
an oxyalkylene group —$(OCH_2CH_2)_n(OCH_2CH(CH_3))_m OR_4$ in which $R_4$ has the same meaning as above, n represents an integer ranging from 1 to 50, and m represents an integer ranging from 0 to 50, providing that at least one of $R_1$, $R_2$ and $R_3$ is a group —OM and that at least one of $R_1$, $R_2$ and $R_3$ is a group —$OR_4$ or —$(OCH_2CH_2)_n(OCH_2CH(CH_3))_mOR_4$.

Preferably, the phosphoric surfactant may be selected from the group consisting of monoester phosphate of alkoxylated fatty alcohol containing from 12 to 20 carbon atoms with from 1 to 50 moles of alkylene oxide selected from ethylene oxide and propylene oxide, and dialkyl phosphates of non-alkoxylated alcohol containing 12 to 22 carbon atoms, and mixtures thereof. The alkyl moiety of the fatty alcohol or the non-alkoxylated alcohol may be a linear or branched, or saturated or unsaturated alkyl group.

More preferably, the phosphoric surfactant may be selected from the group consisting of a combination of ceteth-10 phosphate and dicetyl phosphate, a combination of ceteth-20 phosphate and dicetyl phosphate, and a combination of oleth-5 phosphate and dioleyl phosphate.

As a product including a combination of ceteth-10 phosphate and dicetyl phosphate, mention may be made of CRODAFOS CES, marketed by Croda Inc., U.S.A. As a product including a combination of ceteth-20 phosphate and dicetyl phosphate, mention may be made of CRODAFOS CS-20 ACID, marketed by Croda Inc., U.S.A. As a product including a combination of oleth-5 phosphate and dioleyl phosphate, mention may be made of CRODAFOS HCE, marketed by Croda Inc., U.S.A.

(Non-Ionic Surfactant)

The cosmetic composition according to the present invention includes at least one non-ionic surfactant. The amount of the non-ionic surfactant(s) is not limited. The amount of the non-ionic surfactant(s) can be 0.1 wt % to 10 wt %, preferably 1 wt % to 7 wt %, relative to the total weight of the cosmetic composition.

The non-ionic surfactants may be chosen from monooxyalkylenated or polyoxyalkylenated, monoglycerolated or polyglycerolated nonionic surfactants. The oxyalkylene units are more particularly oxyethylene or oxypropylene units, or a combination thereof, preferably oxyethylene units.

Examples of oxyalkylenated non-ionic surfactants that may be mentioned include:
oxyalkylenated ($C_8$-$C_{24}$)alkylphenols,
saturated or unsaturated, linear or branched, oxyalkylenated $C_8$-$C_{30}$ alcohols,
saturated or unsaturated, linear or branched, oxyalkylenated $C_8$-$C_{30}$ amides,
esters of saturated or unsaturated, linear or branched, $C_8$-$C_{30}$ acids and of polyethylene glycols,
polyoxyethylenated esters of saturated or unsaturated, linear or branched, $C_8$-$C_{30}$ acids and of sorbitol,
saturated or unsaturated, oxyethylenated plant oils,
condensates of ethylene oxide and/or of propylene oxide, inter alia, alone or as mixtures.

The oxyalkylenated non-ionic surfactants may contain a number of moles of ethylene oxide and/or of propylene oxide of between 1 and 50 and preferably between 2 and 30.

In accordance with one preferred embodiment of the invention, the oxyalkylenated non-ionic surfactants are chosen from oxyethylenated $C_8$-$C_{30}$ alcohols.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

in which R represents a linear or branched $C_8$-$C_{40}$ and preferably $C_8$-$C_{30}$ alkyl or alkenyl radical, and m represents a number ranging from 1 to 30 and preferably from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol part of these surfactants may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is particularly preferable to use the $C_8$/$C_{10}$ alcohol containing 1 mol of glycerol, the $C_{10}$/$C_{12}$ alcohol containing 1 mol of glycerol and the $C_{12}$ alcohol containing 1.5 mol of glycerol.

It is preferable that a non-ionic surfactant is selected from the group consisting of polyoxyalkylenated fatty alcohol containing from 12 to 22 carbon atoms with 1 to 50 moles of ethylene oxides, polyoxyalkylenated fatty alcohol containing from 12 to 22 carbon atoms with 1 to 50 moles of propylene oxides, and mixtures thereof.

As examples of the polyoxyalkylenated fatty alcohol containing from 12 to 22 carbon atoms with 1 to 50 moles of ethylene oxides, mention may be made of steareth-2, steareth-20 and ceteareth-2. As examples of the polyoxyalkylenated fatty alcohol containing from 12 to 22 carbon atoms with 1 to 50 moles of propylene oxides, mention may be made of PPG-15 stearyl ether.

(Polyol)

The cosmetic composition according to the present invention includes at least one polyol. The amount of the polyol (s) is not limited. The amount of the polyol(s) can be 2 wt % to 10 wt %, preferably 2 wt % to 6 wt %, relative to the total weight of the cosmetic composition.

The term "polyol" here means a compound which has a plurality of alcohol functions. In other words, polyol is an alcohol having two or more hydroxyl groups. In the scope of this invention, the polyols are without hydrophobic groups such alkyl or alkenyl groups with more than 8 atoms of carbon.

Polyols which can be used in the cosmetic composition of the present invention include, in particular, diols or glycols such as ethyleneglycol, propyleneglycol, butyleneglycol, and hexyleneglycol; polyglycols such as diethyleneglycol, dipropylene glycol, polyethyleneglycol, and polypropyleneglycol; triols such as glycerol; and a mixture thereof.

It is preferable that the polyol is selected from the group consisting of a sugar, a sugar alcohol and a triol.

The term "sugar" here means an oxygen-bearing hydrocarbon-based compound containing several alcohol functions, with or without aldehyde or ketone functions, and which contains at least 4 carbon atoms. These sugars may be monosaccharides, oligosaccharides or polysaccharides.

Examples of suitable sugars that may be mentioned include sucrose (or saccharose), glucose, galactose, ribose, fructose, maltose, mannose, arabinose, xylose, trehalose, and lactose, and derivatives thereof, especially alkyl derivatives, such as methyl derivatives, for instance methylglucose.

The term "sugar alcohol" here means a compound obtained by the reduction of the possible ketone or aldehyde group of a sugar to an alcohol group. Thus, a sugar alcohol has several alcohol functions.

Examples of suitable sugar alcohols that may be mentioned include sorbitol, xylitol, erythritol, pentaerythritol, arabitol, and derivatives thereof.

The term "triol" here means an alcohol which has three hydroxyl groups. An Example of a triol is glycerol or glycerin.

(Oil)

The cosmetic composition according to the present invention includes at least one oil. If two or more oils are used, they may be the same or different. The amount of the oil(s) is not limited. The amount of the oil(s) can be 0.1 wt % to 20 wt %, preferably 4 wt % to 12 wt %, relative to the total weight of the cosmetic composition.

The term "oil" here means an organic compound that is insoluble in water at ordinary temperature (25° C.) and at atmospheric pressure (760 mmHg) (solubility of less than 5%, preferably 1% and even more preferentially 0.1%). In addition, the oils are soluble in organic solvents under the same temperature and pressure conditions, for instance chloroform, ethanol or benzene.

More particularly, the oil is chosen from compounds that are liquid or pasty at room temperature and at atmospheric pressure. Preferably, the oil is a compound that is liquid at a temperature of 25° C. and at atmospheric pressure.

Advantageously, the oils may be chosen from non-silicone fatty substances such as alkanes, fatty alcohols, fatty acids, fatty acid esters, fatty alcohol esters, mineral oils, plant oils, animal oils, synthetic oils, and non-silicone waxes.

Alternatively, the oils may be chosen from silicones.

Preferably, the fatty alcohols, fatty acid esters, fatty alcohol esters, and fatty acids may contain at least one linear or branched, saturated or unsaturated hydrocarbon-based group containing 6 to 30 carbon atoms, which is optionally substituted, in particular with one or more hydroxyl groups (in particular 1 to 4). If they are unsaturated, these compounds may comprise one to three conjugated or non-conjugated carbon-carbon double bonds.

The alkanes, which can comprise from 6 to 30 carbon atoms, may be linear or branched, or possibly cyclic. Examples that may be mentioned include hexane and dodecane.

As oils that may be used in the cosmetic composition according to the present invention, examples that may be mentioned include:

hydrocarbon-based oils of animal origin, such as perhydrosqualene;

hydrocarbon-based oils of plant origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, castor oil, avocado oil, caprylic/capric acid triglycerides, for instance those sold by the company Stearineries Dubois or those sold under the names Miglyol® 810, 812 and 818 by the company Dynamit Nobel, jojoba oil and shea butter oil;

linear or branched hydrocarbons of mineral or synthetic origin, such as volatile or nonvolatile liquid paraffins, and derivatives thereof, petroleum jelly, liquid petroleum jelly, polydecenes, hydrogenated polyisobutene such as Parleam®; isoparaffins, for instance isohexadecane and isodecane;

linear or branched, saturated or unsaturated fatty alcohols containing from 8 to 30 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol; and partially hydrocarbon-based and/or silicone-based fluoro oils, for instance those described in document JP-A-2-295 912; fluoro oils that may also be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The non-silicone wax(es) is (are) chosen from carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the invention are especially marine waxes such as the product sold by the company Sophim under the reference M82, and polyethylene waxes or polyolefin waxes in general.

The fatty acids may be saturated or unsaturated and contain from 6 to 30 carbon atoms and in particular from 9 to 30 carbon atoms. They are more particularly chosen from myristic acid, palmitic acid, stearic acid, behenic acid, oleic acid, linoleic acid, linolenic acid and isostearic acid.

The above esters may be esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate;

lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used. For example, fatty acid triglycerides may be preferably used.

The following may especially be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferable to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The cosmetic composition according to the present invention may also comprise, as a fatty ester, sugar esters and diesters of $C_6$-$C_{30}$ and preferably $C_{12}$-$C_{22}$ fatty acids without alkyleneoxide units. It is recalled that the term "sugar" means oxygen-bearing hydrocarbon-based compounds containing several alcohol functions, with or without aldehyde or ketone functions, and which contain at least 4 carbon atoms. These sugars may be monosaccharides, oligosaccharides or polysaccharides.

Examples of suitable sugars that may be mentioned include sucrose (or saccharose), glucose, galactose, ribose, fructose, maltose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or non-conjugated carbon-carbon double bonds.

The esters according to this variant may also be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, especially, oleo-palmitate, oleo-stearate and palmito-stearate mixed esters.

It is particularly preferable to use monoesters and diesters and especially sucrose, glucose or methylglucose mono- or dioleates, stearates, behenates, oleopalmitates, linoleates, linolenates and oleostearates.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example B370 corresponding to sucrose behenate formed from 20% monoester and 80% di-triester-polyester;
the sucrose mono-dipalmito-stearate sold by the company Goldschmidt under the name Tegosoft® PSE.

The oil may preferably be selected from the group consisting of liquid paraffin, liquid petroleum jelly, polydecenes, liquid esters, and mixtures thereof.

The silicones that may be used in the cosmetic compositions according to the present invention as oils are volatile or nonvolatile, cyclic, linear or branched silicones, which are unmodified or modified with organic groups, having a viscosity from $5 \times 10^{-6}$ to $2.5$ m$^2$/s at 25° C., and preferably $1 \times 10^{-5}$ to $1$ m$^2$/s.

The silicones that may be used in accordance with the present invention may be in the form of oils, waxes, resins or gums.

Preferably, the silicone is chosen from polydialkylsiloxanes, especially polydimethylsiloxanes (PDMS), and organomodified polysiloxanes comprising at least one functional group chosen from poly(oxyalkylene) groups, amino groups and alkoxy groups.

The organopolysiloxanes are defined in greater detail in Walter Noll's "Chemistry and Technology of Silicones" (1968) Academic Press. They can be volatile or nonvolatile.

When they are volatile, the silicones are more particularly chosen from those having a boiling point of between 60° C. and 260° C., and even more particularly from:
(i) cyclic polydialkylsiloxanes containing from 3 to 7 and preferably 4 to 5 silicon atoms. These are, for example, octamethylcyclotetrasiloxane sold in particular under the name Volatile Silicone® 7207 by Union Carbide or Silbione® 70045 V 2 by Rhodia, decamethylcyclopentasiloxane sold under the name Volatile Silicone® 7158 by Union Carbide, and Silbione® 70045 V 5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

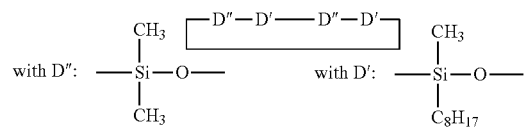

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Nonvolatile polydialkylsiloxanes, polydialkylsiloxane gums and resins, polyorganosiloxanes modified with organofunctional groups above, and mixtures thereof, are preferably used.

These silicones are more particularly chosen from polydialkylsiloxanes, among which mention may be made mainly of polydimethylsiloxanes containing trimethylsilyl end groups. The viscosity of the silicones is measured, for example, at 25° C. according to ASTM standard 445 Appendix C.

Among these polydialkylsiloxanes, mention may be made, in a nonlimiting manner, of the following commercial products:
  the Silbione® oils of the 47 and 70 047 series or the Mirasil® oils sold by Rhodia, for instance the oil 70 047 V 500 000;
  the oils of the Mirasil® series sold by the company Rhodia;
  the oils of the 200 series from the company Dow Corning, such as DC200 with a viscosity of 60 000 mm$^2$/s;
  the Viscasil® oils from General Electric and certain oils of the SF series (SF 96, SF 18) from General Electric.

Mention may also be made of polydimethylsiloxanes containing dimethylsilanol end groups known under the name Dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly ($C_1$-$C_{20}$)dialkylsiloxanes.

The silicone gums that can be used in accordance with the invention are especially polydialkylsiloxanes and preferably polydimethylsiloxanes with high number-average molecular masses of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:
mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
mixtures formed from a polydimethylsiloxane gum with a cyclic silicone, such as the product SF 1214 Silicone Fluid from the company General Electric, wherein this product is an SF 30 gum corresponding to a dimethicone, having a number-average molecular weight of 500 000, dissolved in the oil SF 1202 Silicone Fluid corresponding to decamethylcyclopentasiloxane; and
mixtures of two PDMSs with different viscosities, and more particularly of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. This product preferably contains 15% SE 30 gum and 85% SF 96 oil.

The organopolysiloxane resins that can be used in accordance with the invention are crosslinked siloxane systems containing the following units:
$R_2SiO_{2/2}$, $R_3SiO_{1/2}$, $RSiO_{3/2}$ and $SiO_{4/2}$
in which R represents a hydrocarbon-based group containing 1 to 16 carbon atoms. Among these products, the ones that are particularly preferred are those in which R denotes a $C_1$-$C_4$ lower alkyl radical, more particularly methyl.

Among these resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of the trimethyl siloxysilicate type resins sold in particular under the names X22-4914, X21-5034 and X21-5037 by the company Shin-Etsu.

The organomodified silicones that can be used in accordance with the invention are silicones as defined above and comprising in their structure one or more organofunctional groups attached via a hydrocarbon-based radical.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are chosen particularly from linear and/or branched polydimethyl/methylphenylsiloxanes and polydimethyl/diphenylsiloxanes with a viscosity of from $1 \times 10^{-5}$ to $5 \times 10^{-2}$ m$^2$/s at 25° C.

Among these polyalkylarylsiloxanes, examples that may be mentioned include the products sold under the following names:
the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may be made of polyorganosiloxanes comprising:
  polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 sold by the company Union Carbide, and the ($C_{12}$)alkylmethicone copolyol sold by the company Dow Corning under the name Q2 5200;
  substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;
  alkoxylated groups such as the product sold under the name Silicone Copolymer F-755 by SWS Silicones, and Abil Wax® 2428, 2434 and 2440 by the company Goldschmidt.

Preferably, the oil is a non-silicone liquid fatty substance as described above. In particular, as the non-silicone liquid fatty substance, mention may be made of liquid paraffin, liquid petroleum jelly, polydecenes, liquid esters, and mixtures thereof.

(Alkaline Agent)

The cosmetic composition according to the present invention includes at least one alkaline agent. The amount of the alkaline agent(s) is not limited. The amount of the alkaline agent(s) can be 0.1 wt % to 20 wt %, preferably 1 wt % to 10 wt %, relative to the total weight of the cosmetic composition.

The alkaline agent may be selected from ammonia, alkaline carbonates, alkanolamines, such as mono-, di- and triethanolamines and their derivatives, sodium hydroxide, potassium hydroxide and the compounds of following formula:

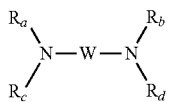

in which W is a propylene residue optionally substituted by a hydroxyl group or a $C_1$-$C_4$ alkyl radical and Ra, Rb, Rc and Rd, which are identical or different, represent a hydrogen atom or a $C_1$-$C_4$ alkyl or $C_1$-$C_4$ hydroxyalkyl radical.

It is preferable that ammonia is used as the alkaline agent. Another alkaline agent may be mixed with ammonia.

(Higher Alcohol)

The cosmetic composition according to the present invention may further include at least one higher alcohol. The amount of the higher alcohol(s) is not limited. The amount of the higher alcohol(s) can be 0.1 wt % to 10 wt %, preferably 1 wt % to 5 wt %, relative to the total weight of the cosmetic composition.

The term "higher alcohol" here means an alcohol having a linear, branched, or cyclic, saturated or unsaturated, $C_8$-$C_{40}$ hydrocarbon group, preferably a $C_8$-$C_{20}$ hydrocarbon group. The $C_8$-$C_{40}$ hydrocarbon group may be a $C_8$-$C_{40}$ alkyl, alkenyl or aralkyl group.

As the higher alcohols preferably used for the present invention, mention may be made of stearyl alcohol and cetearyl alcohol.

(Oxidation Dye)

The cosmetic composition according to the present invention may further include at least one oxidation dye. The oxidation dyes are generally chosen from one or more oxidation bases optionally combined with one or more couplers.

The oxidation bases are chosen, for example, from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-((β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)-pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxy-ethyloxy-para-phenylenediamine, 2,6-dimethyl-para-phenylenediamine, 2,6-diethyl-para-phenylenediamine, 2,3-dimethyl-para-phenylene-diamine, N,N-bis(β-hydroxyethyl)-para-phenylenediamine, 2-chloro-para-phenylenediamine and 2-β-acetylaminoethyloxy-para-phenylene-diamine, and the addition salts thereof with an acid, are particularly preferred.

Among the bis(phenyl)alkylenediamines that may be mentioned, for example, are N,N'-bis(β-hydroxyethyl)-N,N'-bis (4'-aminophenyl)-1,3-diaminopropanol, N,N'-bis(β-hydroxyethyl)-N,N'-bis(4'-amino-phenyl)ethylenediamine, N,N'-bis(4-aminophenyl)tetramethylene-diamine, N,N'-bis (β-hydroxyethyl)-N,N'-bis(4-aminophenyl)tetra-methylenediamine, N,N'-bis(4-methylaminophenyl)tetra-methylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethyl-phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxy-phenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a] pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo

[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]-pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-l-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used.

A heterocyclic base that may also be used is 2,3-diamino-6,7-dihydro-1H,5H-pyrazolo[1,2-a]pyrazol-1-one or a salt thereof.

The composition according to the invention may optionally comprise one or more couplers advantageously chosen from those conventionally used in the dyeing of keratin fibres.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazo-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially chosen from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.0001% to 10% by weight relative to the total weight of the composition, and preferably from 0.005% to 5% by weight relative to the total weight of the composition.

The content of coupler(s), if it is (they are) present, advantageously represents from 0.0001% to 10% by weight relative to the total weight of the composition, and preferably from 0.005% to 5% by weight relative to the total weight of the composition.

(Direct Dye)

The cosmetic composition according to the present invention may further include at least one direct dye of nonionic, cationic or anionic nature, which may be chosen, for example, from the following red or orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)-benzene,
1-(β,γ-dihydroxypropyl)oxy-3-nitro-4-(β-hydroxyethy-1)-aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine and
1-amino-2-nitro-4-hydroxy-5-methylbenzene.

The cosmetic composition according to the present invention may also comprise, in addition to or in replacement for these nitrobenzene dyes, one or more additional direct dyes chosen from yellow, green-yellow, blue or violet nitrobenzene dyes, azo dyes, anthraquinone dyes, naphthoquinone dyes, benzoquinone dyes, indigoid dyes, and triarylmethane-based dyes.

These additional direct dyes may especially be basic dyes, among which mention may be made more particularly of the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99", or acidic direct dyes, among which mention may be made more particularly of the dyes known in the Color Index, 3rd edition, under the names "Acid Orange 7", "Acid Orange 24", "Acid Yellow 36", "Acid Red 33", "Acid Red 184", "Acid Black 2", "Acid Violet 43" and "Acid Blue 62", or alternatively cationic direct dyes such as those described in WO 95/01772, WO 95/15144 and EP-A-0 714954, the content of which forms an integral part of the present invention.

Among the additional yellow and green-yellow nitrobenzene direct dyes that may be mentioned, for example, are the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(βp-hydroxyethyl)amino-4-nitro-6-chlorobenzene,
1-amino-2-nitro-6-methylbenzene,
1-(β-hydroxyethyl)amino-2-hydroxy-4-nitrobenzene, N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene and
4-(β-hydroxyethyl)amino-3-nitrobenzamide.

Among the additional blue or violet nitrobenzene direct dyes that may be mentioned, for example, are the compounds chosen from:
1-(β-hydroxyethyl)amino-4-N,N-bis(β-hydroxyethyl)amino-2-nitrobenzene,
1-(γ-hydroxypropyl)amino-4,N,N-bis(β-hydroxyethyl)amino-2-nitrobenzene,
1-(β-hydroxyethyl)amino-4-(N-methyl-N-β-hydroxy-ethyl)amino-2-nitrobenzene,
1-(β-hydroxyethyl)amino-4-(N-ethyl-N-β-hydroxyethyl)amino-2-nitrobenzene,
1-(β,β-dihydroxypropyl)amino-4-(N-ethyl-N-β-hydroxyethyl)amino-2-nitrobenzene,
2-nitro-para-phenylenediamines having the following formula:

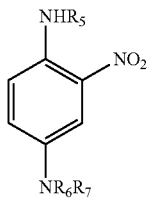

in which:
$R_6$ represents a $C_{1-c4}$ alkyl radical or a β-hydroxy-ethyl, β-hydroxypropyl or γ-hydroxypropyl radical;
$R_5$ and $R_7$, which may be identical or different, represent a β-hydroxyethyl, β-hydroxypropyl, γ-hydroxypropyl or β,γ-dihydroxypropyl radical, at least one of the radicals $R_6$, $R_7$ or $R_5$ representing a γ-hydroxypropyl radical and $R_6$ and $R_7$ not simultaneously being able to denote a β-hydroxyethyl radical when $R_6$ is a γ-hydroxypropyl radical, such as those described in FR 2 692 572.

When they are present, the direct dye(s) preferably represent(s) from 0.0005% to 12% by weight approximately relative to the total weight of the cosmetic composition, and even more preferably from 0.005% to 6% by weight approximately relative to the total weight.

(Reducing Agent)

The cosmetic composition according to the present invention may further include at least one reducing agent. The reducing agents are generally chosen from sulfured compounds and non-sulfured compounds.

The sulfured compounds are generally chosen from thiols, sulfites and hydrosulfites. Thiols are preferably selected from thioglycolic acid or thiolactic acid or cysteine and their salts.

The non-sulfured compounds are generally chosen from reductones, especially ascorbic acid or erythorbic acid and their salts.

When they are present, the reducing agent(s) preferably represent(s) from 0.0005% to 20% by weight approximately relative to the total weight of the cosmetic composition, and even more preferably from 0.05% to 10% by weight approximately relative to the total weight.

(Cosmetic Composition)

The cosmetic composition according to the present invention can be used for cosmetic treatment for keratin fibers such as hair. For example, the cosmetic composition according to the present invention can be used for coloring keratin fibers or reshaping keratin fibers.

Advantageously, the cosmetic composition according to the present invention is in the form of a gel or a cream.

The cosmetic composition for coloring keratin fibers according to the present invention may contain various adjuvants conventionally used in hair compositions, such as anionic, cationic, nonionic, amphoteric or zwitterionic polymers or mixtures thereof; mineral thickeners, and in particular fillers such as clays, talc; organic thickeners with, in particular, anionic, cationic, nonionic and amphoteric polymeric associative thickeners; penetrants; ionic surfactants such as cationic, zwitterionic surfactants, sequestrants; fragrances; dispersants; film-forming agents; ceramides; preserving agents; and opacifiers.

Each of the above adjuvants is generally present in an amount of them of between 0.01% and 20% by weight relative to the weight of cosmetic composition according to the present invention.

When the composition is used in order to dye keratin fibers, the coloring process for keratin fibers can be performed by, first, mixing the cosmetic composition according to the present invention with a developer comprising one or more oxidizing agents. The mixing ratio of the cosmetic composition according to the present invention and the developer may be 1:1 to 1:1.5.

More particularly, the oxidizing agent(s) is (are) chosen from hydrogen peroxide, urea peroxide, alkali metal bromates or ferricyanides, and peroxygenated salts, for instance alkali metal or alkaline-earth metal persulfates, perborates and percarbonates, and peracids and precursors thereof.

The oxidizing agent is advantageously constituted by hydrogen peroxide, especially as an aqueous solution (aqueous hydrogen peroxide solution), the concentration of which may range from 1 to 50 wt % and preferably from 5 to 40 wt %.

As a function of the desired degree of lightening, the developer may also comprise an oxidizing agent preferably chosen from peroxygenated salts.

The developer may be aqueous or nonaqueous. The term "aqueous" means that the developer comprises more than 5% by weight of water, preferably more than 10% by weight of water and even more advantageously more than 20% by weight of water.

Usually, the pH of the developer, when it is aqueous, is less than 7.

The developer may also contain other ingredients conventionally used in the field, especially those detailed previously in the context of the cosmetic composition according to the present invention.

The developer is in various forms, for instance a solution, an emulsion or a gel.

Next, the mixture of the cosmetic composition according to the present invention and the developer is applied onto keratin fibers such as hair, and washed out after appropriate processing time. As a result, the keratin fibers such as hair can be colored.

On the other hand, the cosmetic composition for reshaping keratin fibers according to the present invention typically contains a reducing agent, such as thioglycolic acid, for breaking a disulfide bond in the keratin fibers. The cosmetic composition for reshaping keratin fibers according to the present invention may also contain various adjuvants as mentioned above. Each of the above adjuvants are generally present in an amount of between 0.01% and 20% by weight relative to the weight of cosmetic composition according to the present invention.

The reshaping process for keratin fibers according to the present invention may be performed as follows.

First, keratin fibers are subjected to mechanical tension for deformation. The mechanical tension can be applied to the keratin fibers by any means to deform the keratin fibers to an intended shape. For example, the mechanical tension may be provided by at least one reshaping means selected from the group consisting of a curler, a roller, a plate and an iron. The reshaping means may comprise at least one heater.

Next, the cosmetic composition for reshaping keratin fibers according to the present invention is applied to the keratin fibers. Thus, a disulfide bond in the keratin fibers is broken. The application of the composition may be performed by any means, such as a brush and a comb. The keratin fibers to which the mechanical tension has been applied should be treated with the composition.

Next, an oxidizing composition comprising one or more oxidizing agents as described above is applied onto the keratin fibers to form a disulfide bond again. As a result, the keratin fibers such as hair can be reshaped.

The keratin fibers may be rinsed after the step of applying the cosmetic composition according to the present invention onto the keratin fibers and/or after the step of heating the keratin fibers.

If necessary, the cosmetic composition according to the present invention may be applied to keratin fibers before and/or during the application of mechanical tension to the keratin fibers.

Another subject-matter of the invention is a dyeing kit or multicompartment device in which a first compartment includes the dyeing composition of the present invention defined above and a second compartment includes an oxidizing agent. This device can be equipped with a means allowing the desired mixture to be deposited on the hair, such as the devices described in Patent FR-2 586 913 on behalf of the Applicant Company.

EXAMPLES

The present invention will be described in more detail by way of examples, which however should not be construed as limiting the scope of the present invention.

Examples 1 to 4 and Comparative Examples 1 to 5

The following compositions according to Examples 1 to 4 and Comparative Examples 1 to 5 were prepared by mixing the components shown in Table 1. The numerals in Table 1 mean percent by weight.

It should be noted that Crodafos CS-20 Acid marketed by Croda Inc., U.S.A., was used as a mixture of cetearyl alcohol, dicetyl phosphate and ceteth-20 phosphate, and that Crodafos HCE marketed by Croda Inc., U.S.A., was used as a mixture of oleth-5 phosphate and dioleyl phosphate.

TABLE 1

|  | Ex. 1 | Ex. 2 | Ex. 3 | Ex. 4 | Comp. Ex. 1 | Comp. Ex. 2 | Comp. Ex. 3 | Comp. Ex. 4 | Comp. Ex. 5 |
| --- | --- | --- | --- | --- | --- | --- | --- | --- | --- |
| Steareth-2 | 1.500 | 1.500 | 1.500 | 1.500 | 1.500 | 1.500 | — | 1.500 | 1.500 |
| Steareth-20 | 1.000 | 1.000 | 1.000 | 1.000 | 1.000 | 1.000 | — | 1.000 | 1.000 |
| Ceteareth-2 | — | — | — | — | 2.000 | 1.500 | — | — | — |
| PPG-15 stearyl ether | 1.500 | 1.500 | 1.500 | 1.500 | 1.500 | — | — | 1.500 | 1.500 |
| Cetearyl alcohol | 9.625 | 9.625 | 9.250 | 8.000 | 10.000 | 10.000 | 9.625 | 9.625 | 9.625 |
| Dicetyl phosphate | 0.500 | 0.500 | 0.375 | — | — | — | 0.500 | 0.500 | 0.500 |
| Ceteth-10 phosphate | 0.375 | 0.375 | — | — | — | — | 0.375 | 0.375 | 0.375 |
| Ceteth-20 phosphate | — | — | 0.875 | — | — | — | — | — | — |
| Oleth-5 phosphate | — | — | — | 1.500 | — | — | — | — | — |
| Dioleyl phosphate | — | — | — | 1.000 | — | — | — | — | — |
| Liquid paraffin | 8.000 | 8.000 | 8.000 | 8.000 | 8.000 | 8.000 | 8.000 | — | 8.000 |
| Sorbitol | 4.000 | — | 4.000 | 4.000 | 4.000 | 4.000 | 4.000 | 4.000 | — |
| Glycerin | — | 4.00 | — | — | — | — | — | — | — |
| Pentasodium pentetate (40%) | 0.200 | 0.200 | 0.200 | 0.200 | 0.200 | 0.200 | 0.200 | 0.200 | 0.200 |
| Erythorbic acid | 0.500 | 0.500 | 0.500 | 0.500 | 0.500 | 0.500 | 0.500 | 0.500 | 0.500 |
| Sodium metabisulfite | 0.500 | 0.500 | 0.500 | 0.500 | 0.500 | 0.500 | 0.500 | 0.500 | 0.500 |
| p-Phenylenediamine | 0.500 | 0.500 | 0.500 | 0.500 | 0.500 | 0.500 | 0.500 | 0.500 | 0.500 |
| p-Aminophenol | 0.160 | 0.160 | 0.160 | 0.160 | 0.160 | 0.160 | 0.160 | 0.160 | 0.160 |
| Resorcinol | 0.500 | 0.500 | 0.500 | 0.500 | 0.500 | 0.500 | 0.500 | 0.500 | 0.500 |
| m-Aminophenol | 0.110 | 0.110 | 0.110 | 0.110 | 0.110 | 0.110 | 0.110 | 0.110 | 0.110 |
| 2-Methyl-5-hydroxyethylaminophenol | 0.100 | 0.100 | 0.100 | 0.100 | 0.100 | 0.100 | 0.100 | 0.100 | 0.100 |
| 4-Amino-2-hydroxytoluene | 0.030 | 0.030 | 0.030 | 0.030 | 0.030 | 0.030 | 0.030 | 0.030 | 0.030 |
| Perfume | 0.400 | 0.400 | 0.400 | 0.400 | 0.400 | 0.400 | 0.400 | 0.400 | 0.400 |
| Ammonia (25%) | 7.040 | 7.040 | 7.040 | 7.040 | 7.040 | 7.040 | 7.040 | 7.040 | 7.040 |
| Ethanolamine | 0.250 | 0.250 | 0.250 | 0.250 | — | — | 0.250 | 0.250 | 0.250 |
| Deionized water | BL | BL | BL | BL | BL | BL | BL | BL | BL |

BL: Balance

For each of Examples 1 to 4 and Comparative Examples 1 to 5, the evaporation of ammonia was evaluated by mixing with a developer, the composition of which is shown in Table 2, and by performing a sniff test and a chemi-luminescence test as described below.

TABLE 2

|  | Wt % |
|---|---|
| Liquid paraffin | 0.8 |
| Stearyl alcohol | 0.7 |
| Cetyl alcohol | 0.7 |
| Myristyl alcohol | 2.8 |
| Ceteareth-33 | 1.7 |
| Beheneth-10 | 0.5 |
| Cocamidopropyl betaine 35%) | 0.143 |
| Hydrogen peroxide (50%) | 11.7 |
| Sodium pyrophosphate | 0.04 |
| Sodium salicylate | 0.035 |
| Sodium etidronate | 0.2 |
| Phosphoric acid | qs to adjust pH |
| Water | balance |

[Sniff Test]

5 panels conducted sensory evaluation by directly sniffing the mixture of any of Examples 1 to 4 and Comparative Examples 1 to 5 with the above developer, and scored in accordance with the following criteria.

1: Ammonia odor was very weak
2: Ammonia odor was weak
3: Ammonia odor was medium
4: Ammonia odor was strong
5: Ammonia odor was very strong The scores by the panels were collected, and the average score for each of Examples 1 to 4 and Comparative Examples 1 to 5 was statistically calculated. The results are shown in Tables 3 and 4.

TABLE 3

|  | Ex. 1 | Ex. 2 | Ex. 3 | Ex. 4 |
|---|---|---|---|---|
| Average Score | 1 | 1 | 1 | 1 |

TABLE 4

|  | Comp. Ex. 1 | Comp. Ex. 2 | Comp. Ex. 3 | Comp. Ex. 4 | Comp. Ex. 5 |
|---|---|---|---|---|---|
| Average Score | 4 | 5 | 5 | 5 | 4 |

Examples 1 to 4 show better results in ammonia trapping ability as compared to Comparative Examples 1 to 5.

[Chemi-Luminescence Test]

The concentration of ammonia evaporated from the mixture of any of Examples 1 to 4 and Comparative Examples 1 to 5 with the above developer was determined by using a chemi-luminescence detecting system (CLD 822 CMI by Eco Physics AG, Switzerland). The highest peak concentration (Vmax) was used for determining the concentration of ammonia evaporated from the mixture. The results are shown in Tables 5 and 6.

TABLE 5

|  | Ex. 1 | Ex. 2 | Ex. 3 | Ex. 4 |
|---|---|---|---|---|
| Ammonia Concentration (ppm) | 234 | 283 | 256 | 288 |

TABLE 6

|  | Comp. Ex. 1 | Comp. Ex. 2 | Comp. Ex. 3 | Comp. Ex. 4 | Comp. Ex. 5 |
|---|---|---|---|---|---|
| Ammonia Concentration (ppm) | 459 | 743 | 689 | 872 | 532 |

Examples 1 to 4 show better results in ammonia evaporation as compared to Comparative Examples 1 to 5.

The invention claimed is:

1. A cosmetic composition, comprising:
   (a) at least one phosphoric surfactant selected from the group consisting of:
       a monoester phosphate of an alkoxylated fatty alcohol comprising from 12 to 20 carbon atoms with 1 to 50 moles of ethylene oxide, and propylene oxide, or a mixture thereof; and
       a dialkyl phosphate of a non-alkoxylated alcohol comprising 12 to 22 carbon atoms;
   (b) at least one non-ionic surfactant selected from the group consisting of a polyoxyalkylenated fatty alcohol comprising from 12 to 22 carbon atoms with 1 to 50 moles of ethylene oxide, and a polyoxyalkylenated fatty alcohol comprising from 12 to 22 carbon atoms with 1 to 50 moles of propylene oxide;
   (c) a polyol;
   (d) an oil, which is a non-silicone liquid fatty substance; and
   (e) an alkaline agent.

2. The composition of claim 1, wherein the phosphoric surfactant is selected from the group consisting of a combination of ceteth-10 phosphate and dicetyl phosphate, a combination of ceteth-20 phosphate and dicetyl phosphate, and a combination of oleth-5 phosphate and dioleyl phosphate.

3. The composition of claim 1, wherein the polyol is selected from the group consisting of a sugar, a sugar alcohol and a triol.

4. The composition of claim 1, wherein the oil is at least one selected from the group consisting of liquid paraffin, liquid petroleum jelly, a polydecene, and a liquid ester.

5. The composition of claim 1, wherein the alkaline agent is ammonia.

6. The composition of claim 1, further comprising a higher alcohol.

7. The composition of claim 1, further comprising an oxidation dye.

8. The composition of claim 7, wherein the oxidation dye is at least one selected from the group consisting of an oxidation base and a coupler.

9. The composition of claim 1, further comprising a direct dye.

10. The composition of claim 1, further comprising a reducing agent.

11. The composition of claim 1, which is suitable for coloring keratin fibers.

12. The composition of claim 1, which is suitable for reshaping keratin fibers.

* * * * *